(12) United States Patent
Matsuya

(10) Patent No.: US 6,933,512 B2
(45) Date of Patent: Aug. 23, 2005

(54) CHARGED PARTICLE BEAM INSTRUMENT

(75) Inventor: Miyuki Matsuya, Tokyo (JP)

(73) Assignee: Jeol Ltd., Tokyo (JP)

( * ) Notice: Subject to any disclaimer, the term of this patent is extended or adjusted under 35 U.S.C. 154(b) by 169 days.

(21) Appl. No.: 09/798,881

(22) Filed: Mar. 2, 2001

(65) Prior Publication Data

US 2001/0032931 A1 Oct. 25, 2001

(30) Foreign Application Priority Data

Mar. 2, 2000 (JP) .......................................... 2000-56602

(51) Int. Cl.[7] .......................................... H01J 37/065
(52) U.S. Cl. ........................ 250/492.22; 250/492.1; 250/491.1; 250/492.21; 250/311
(58) Field of Search ................ 250/305–307, 250/310–311, 492.2, 492.21, 492.22, 492.3, 491.1, 492.1, 398, 396 ML, 396 R

(56) References Cited

U.S. PATENT DOCUMENTS

| | | | | |
|---|---|---|---|---|
| 4,851,844 A | * | 7/1989 | Akagiri | 341/150 |
| 4,990,778 A | * | 2/1991 | Norioka | 250/310 |
| 5,404,012 A | * | 4/1995 | Yamada | 250/310 |
| 5,767,515 A | * | 6/1998 | Honda | 250/310 |
| 5,933,217 A | * | 8/1999 | Nakasuji et al. | 355/53 |

FOREIGN PATENT DOCUMENTS

JP 1183044 * 7/1989 ............ H01J/37/04

* cited by examiner

*Primary Examiner*—John R. Lee
*Assistant Examiner*—David A. Vanore
(74) *Attorney, Agent, or Firm*—The Webb Law Firm

(57) ABSTRACT

A charged particle beam instrument capable of reducing the spread of the probe diameter while maintaining the probe current constant. An electrical current $I_d$ is detected by a detection aperture to create a feedback signal. The feedback signal is supplied to a condenser lens control and to an objective lens control via a signal adjuster. The objective lens control portion controls the objective lens such that the charged particle probe is in focus.

6 Claims, 3 Drawing Sheets

CHARGED PARTICLE BEAM INSTRUMENT

BACKGROUND OF THE INVENTION

1. Field of the Invention

The present invention relates to a charged particle beam instrument, such as an electron probe microanalyzer or a scanning electron microscope.

2. Description of the Related Art

In a charged particle beam instrument, such as an electron probe microanalyzer or a scanning electron microscope, a charged particle beam emitted from a charged particle beam source is accelerated and focused onto a specimen by a condenser lens system and an objective lens. As the charged particle beam hits the specimen, X-rays and secondary particles are produced, and these are detected.

In this kind of instrument, the current of the charged particle probe made to hit the specimen is stabilized. FIG. 1 is a diagram schematically illustrating this probe current-stabilizing function. A charged particle beam CB produced by a charged particle beam source (not shown) and accelerated is sharply focused onto a specimen 3 by a condenser lens system 1 and an objective lens 2.

A detection aperture 4 is located between the condenser lens system 1 and the objective lens 2 and detects an outer portion of the charged particle beam. The output signal from the detection aperture 4 is amplified by a feedback device 5 and supplied to a control portion 6 for the condenser lens system 1 for adjusting the probe current.

The control portion 6 adjusts the strength of the condenser lens system 1 according to the magnitude of a reference signal and the magnitude of the output signal from the feedback device 5. A feedback loop is formed in this way. Therefore, the current of the charged particle beam probe P impinging on the specimen 3 can be kept constant in principle if the current density of the charged particle beam does not vary.

To establish negative feedback (i.e., to prevent positive feedback as described in Japanese Patent Laid-Open No. 183044/1989), an aperture for limiting peripheral portions of a charged particle beam exiting from the condenser lens system is placed ahead of the detection aperture 4 as described in Japanese Technical Review 82-7798. This aperture is omitted in FIG. 1.

The detection aperture 4 can also be designed to act also as an objective aperture for controlling the probe current and the divergence angle of the probe.

As mentioned previously, where negative feedback is applied to the condenser lens system 1, if the exciting current supplied to the condenser lens system 1 is varied so as not to vary the probe current, the position of the focal point of the condenser lens system 1 automatically changes from the state indicated by the solid line to the state indicated by the broken line. It is now assumed that some change occurs in the charged particle beam source and that the probe current should vary from $I_p$ by $\Delta I_p$. However, the negative feedback varies the distance between the detection aperture 4 and the focal point, thus maintaining the probe current $I_p$ constant.

In spite of this, an adjustment of the condenser lens system 1 moves the focal position of the charged particle probe P on the specimen out of the specimen surface by $\Delta b$. The spread portion $\Delta d_{1p}$ of the probe diameter due to the feedback adds to the final probe diameter $d_p$.

It is assumed that the objective lens 2 has an object distance of a and an image distance of b. If the focal distance $f_{OL}$ of the objective lens 2 is constant, the following relation holds:

$$db/da = -M^2$$

where $M$ ($=b/a$) is the magnification of the objective lens. Therefore, when the object distance varies by a small distance of $\Delta a$, the image distance deviates by $\Delta b$, which is given by:

$$\Delta b = -M^2 \cdot \Delta a$$

That is, the image distance deviation $\Delta b$ can be reduced by combining the lenses so as to reduce the magnification $M$ ($=b/a$). It can be seen, however, that the deviation $\Delta b$ cannot be reduced to any desired small value, because the number of lenses is finite, and because the microscope column has a finite length.

On the other hand, in an instrument equipped with a charged particle beam source of low brightness, the final probe diameter $d_p$ is not thin. Therefore, the spread $\Delta d_{1p}$ of the probe diameter due to negative feedback presents no serious problems. In contrast, emission of a charged particle beam from a charged particle beam source of high brightness (e.g., field emission, electron emission, such as Schottky emission, and ion emission due to field ionization or electrolytic dissociation) can produce a quite thin final probe diameter $d_p$. Consequently, the spread $\Delta d_{1p}$ of the probe diameter due to negative feedback can no longer be neglected.

Furthermore, in a charged particle beam source of high brightness, the emission current tends to vary. This increases the amount of correction made by negative feedback. This, in turn, increases the spread $\Delta d_{1p}$ of the probe diameter, thus increasing the amount of defocus.

A charged particle beam source of high brightness is adopted to obtain a small probe diameter. This object cannot be achieved due to the spread $\Delta d_{1p}$ of the probe diameter, which, in turn, is caused by negative feedback that is used to obtain a stable probe current.

SUMMARY OF THE INVENTION

It is an object of the present invention to provide a charged particle beam instrument capable of reducing the spread of the probe diameter greatly while maintaining the probe current constant.

This object is achieved by a charged particle beam instrument that has a charged particle beam source for producing a charged particle beam having a probe current, a first focusing means for focusing the charged particle beam and varying the probe current of the charged particle beam impinging on a specimen, a second focusing means for varying the degree of focus of the charged particle beam impinging on the specimen, a first control portion for controlling the first focusing means, and a second control portion for controlling the second focusing means. This charged particle beam instrument is characterized in that it is equipped with a means for detecting a part of the current of the charged particle beam from the charged particle beam source to thereby produce a detected signal, controlling the control portion for the first focusing means to maintain constant the probe current of the charged particle beam impinging on the specimen, and controlling the control portion for the second focusing means according to the detected signal to adjust the focus of the charged particle beam.

Other objects and features of the invention will appear in the course of the description thereof, which follows.

DESCRIPTION OF THE PREFERRED EMBODIMENT

Figure 1:
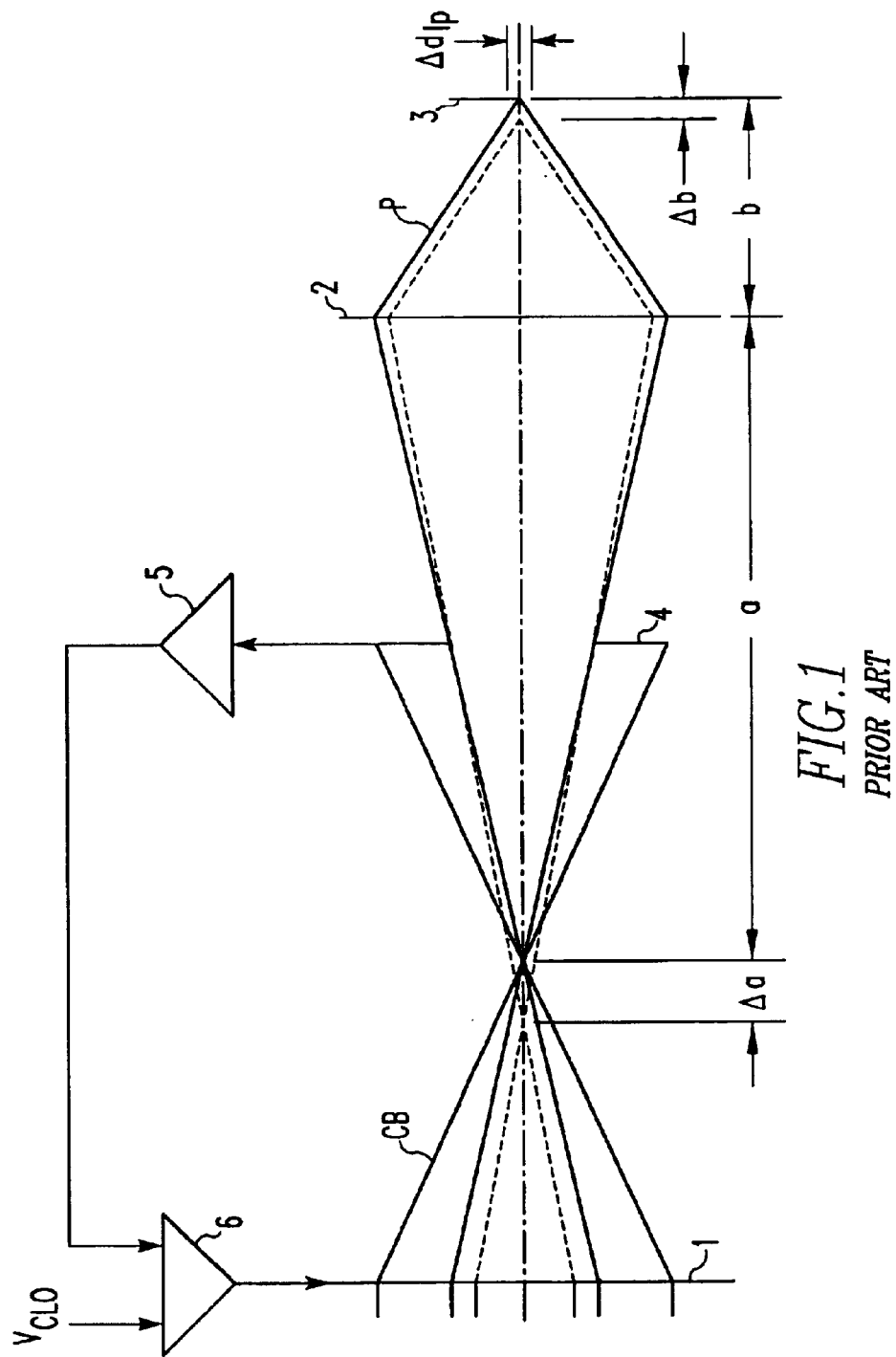
FIG. 1 is a diagram illustrating the prior art charged particle beam instrument.
Figure 2:
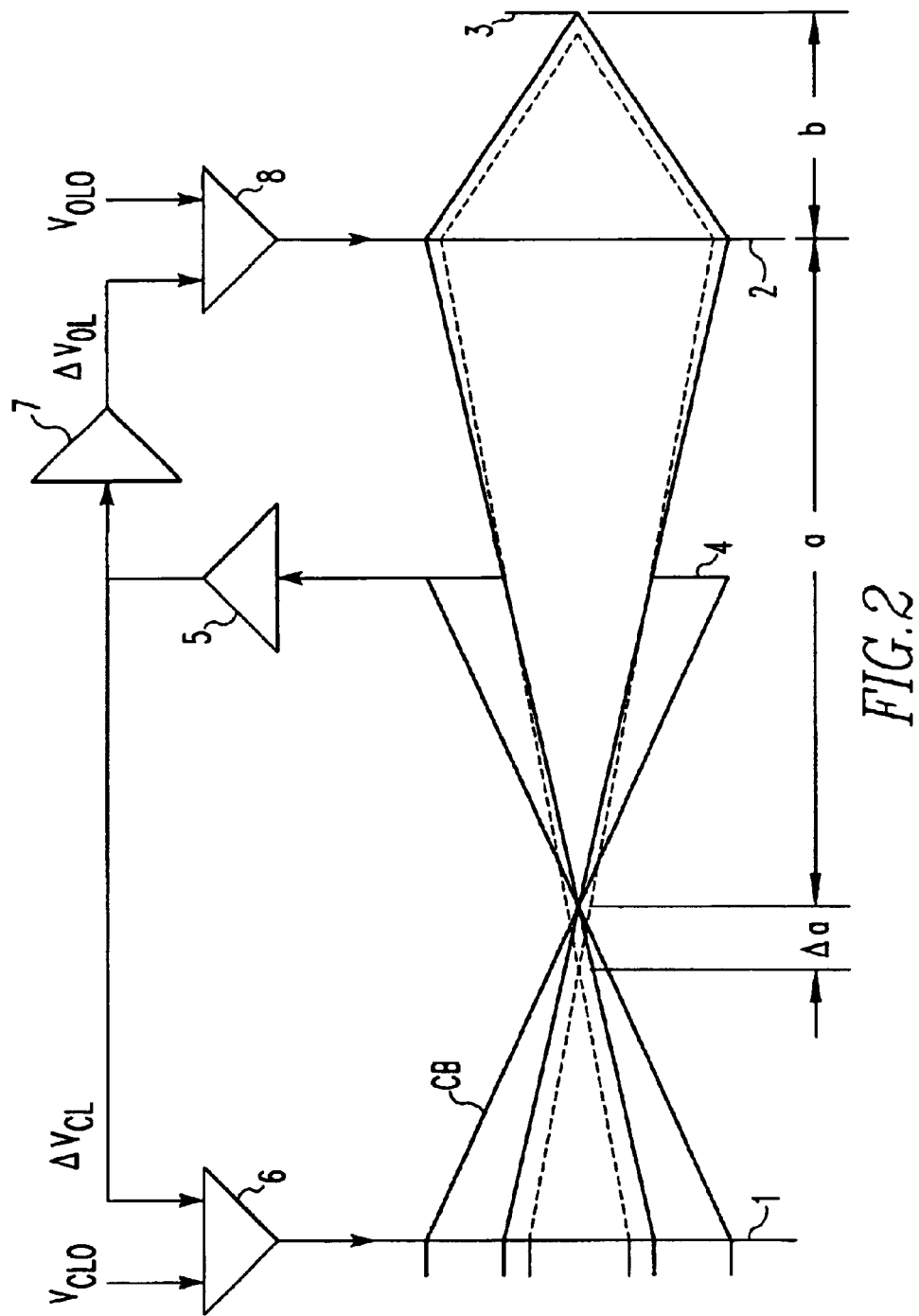
FIG. 2 is a diagram illustrating the fundamental structure of a charged particle beam instrument in accordance with the present invention.

An embodiment of the present invention is hereinafter described in detail by referring to the accompanying drawings. FIG. 2 shows the fundamental structure of a charged particle beam instrument in accordance with the present invention. Like components are indicated by like reference numerals in various figures including FIG. 1 used to describe the prior art structure. Those components which have been already described will not be described below.

Referring to FIG. 2, a detection aperture 4 detects an electrical current $I_d$. A feedback device 5 converts the detected current $I_d$ into a voltage and creates a signal for feedback (referred to as the "feedback signal" herein). The output signal from the feedback device 5 is fed to a condenser lens control portion 6 and to an objective lens control portion 8 via a signal adjuster 7. The objective lens control portion 8 compares the feedback signal whose amplitude is adjusted by the signal adjuster 7 with an objective lens control signal and controls the strength of the objective lens 2 according to the result of the comparison.

To establish this negative feedback, an aperture (not shown in FIG. 2) is mounted between the condenser lens system 1 and the detection aperture 4 to limit peripheral portions of the charged particle beam exiting from the condenser lens system 1.

The operation of the instrument of the construction described thus far is next described. Let $V_{CL}$ (=$V_{CLO}$) be an input signal applied to the condenser lens control portion 6 before applying negative feedback to it. Let $V_{OL}$(=$V_{OLO}$) be an input signal applied to the objective lens control portion 8. The following signals corresponding to these input signals are applied to the condenser lens system 1 and the objective lens 2, respectively.

$$I_{CL}=\rho_{CL} \cdot V_{CL}$$

$$I_{OL}=\rho_{OL} \cdot V_{OL}$$

where $\rho_{CL}$ and $\rho_{OL}$ are constants. Where the lenses are of the electrostatic type, $I_{CL}$ and $I_{OL}$ correspond to voltages. Where the lenses are of the magnetic type, they correspond to exciting currents.

Negative feedback is applied by the detection aperture 4, the feedback device 5, the condenser lens control portion 6, and the condenser lens system 1 such that the current $I_d$ detected by the detection aperture 4 is kept substantially constant if the detected current $I_d$ increases monotonously when the probe current $I_p$ increases. The conditions under which negative feedback is established are described, for example, in the above-cited Japanese Patent Laid-Open No. 183044/1989. The operation is described in further detail.

First, a state in which negative feedback is not applied is discussed. It is assumed that some change has occurred in a particle source, resulting in the following changes:

$$I_{pO} \rightarrow I_{pO} + \Delta I_p$$

$$I_{dO} \rightarrow I_{dO} + \Delta I_d$$

It is first assumed that a signal $\Delta V_{CL}$ is added to the condenser lens control portion 6 to return the probe current to its original value $I_{pO}$ and that the position of the focal point of the condenser lens system 1 has been varied thereby. Then, a signal $\Delta V_{OL}$ is applied to the objective lens control portion 8 to prevent the degree of focus of the particle probe from being varied by the change $\Delta a$ in the object distance. These signals $\Delta V_{CL}$ and $\Delta V_{OL}$ should be applied to the condenser lens control portion 6 and the objective lens control portion 8, respectively, by some method to maintain constant the degree of focus of the particle probe while maintaining constant the probe current and the detected current.

A state in which negative feedback is applied is next discussed. Under the presence of negative feedback, some cause on the side of the charged particle beam attempts to vary the probe current $I_p$ and the detected current $I_d$. However, these are kept almost constant because of negative feedback applied by the feedback device 5 to the condenser lens control portion 6.

If the probe current $I_p$ and the detected current $I_d$ are kept constant, the signal applied to the condenser lens control portion 6 from the feedback device 5 should be equal to the above-described $\Delta V_{CL}$, as can be seen from the description provided above. To obtain normal negative feedback operation, the amplification degree of the feedback device 5 with respect to the signal from the detection aperture 4 is designed to have a sufficiently large value. Therefore, this signal $\Delta V_{CL}$ is created.

On the other hand, the signal created by negative feedback is $\Delta V_{CL}$. This signal is amplified or attenuated, and the signal adjuster 7 is so operated that the resulting signal is equal to the aforementioned signal $\Delta V_{OL}$. The operation of the signal adjuster 7 may be determined according to the state of the operating charged particle beam instrument (e.g., the energy E of the particle beam, the probe current $I_p$, and the image distance b of the objective lens 2).

The signal adjuster 7 may be so designed that its output is in proportion to the input signal $\Delta V_{CL}$ (linear output). If necessary, the following nonlinear calculations may be involved.

$$(\Delta V_{CL})^n (n=0, 1, 2, \ldots)$$

$$\sin(n \cdot k \Delta V_{CL})(n=0, 1, 2, \ldots; k \text{ is a constant})$$

The general fundamental structure and the principle of operation have been described thus far. A more specific example is described below by referring to FIG. 3, which shows a modification of the feedback device 5 and a modification of the signal adjuster 7, it being noted that the feedback device 5 and the signal adjuster 7 are shown in FIG. 2.

Figure 3:
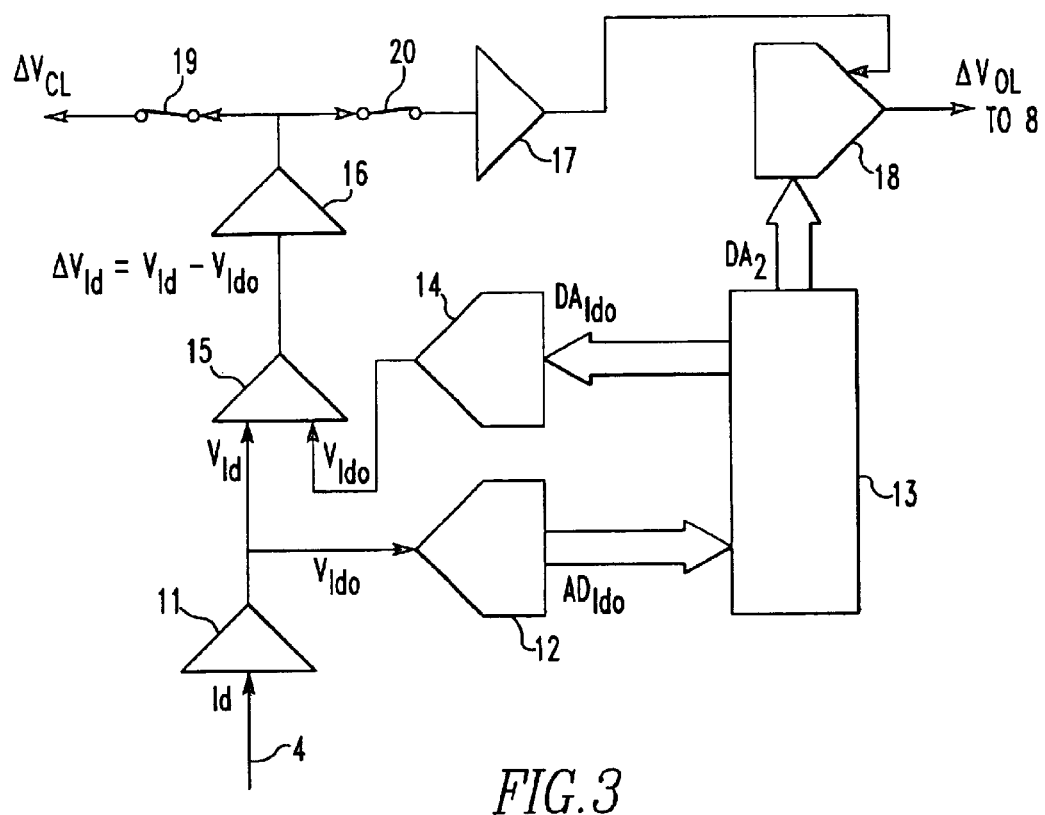
FIG. 3 is a diagram showing one specific example of a feedback signal-processing circuit.

In the configuration of FIG. 3, if an instruction for start of stabilization of the probe current is given from the outside, the current $I_d = I_{dO}$ of the charged particle beam detected by the detection aperture 4 is converted into a signal voltage by a current-to-voltage converter 11 immediately before negative feedback is applied to the condenser lens system 1.

The output signal $V_{1d} = V_{1d0}$ from the current-to-voltage converter 11 is applied to an A/D converter 12 that converts an analog signal into a digital signal. The A/D converter 12 sends data $AD_{1d0}$ corresponding to the $V_{1d0}$ to the control portion 13. The control portion 13 saves this data and sends data $DA_{1d0}$ to a D/A converter 14 that converts a digital signal to an analog signal.

The output from the D/A converter 14 remains the same as the output $V_{1d0}$ from the current-to-voltage converter 11 immediately before application of negative feedback until a next instruction for start of stabilization of the probe current is given. Then, the output $V_{1d}$ from the current-to-voltage converter 11 and the output $V_{1d0}$ from the D/A converter 14 are applied to an adder 15, which, in turn, produces the difference $\Delta V_{1d}(=V_{1d}-V_{1d0})$ between them.

The output from the adder 15 is applied to an amplifier 16 whose gain can be set to a sufficiently large value A1. Immediately before application of negative feedback, the difference $\Delta V_{1d}=0$. When negative feedback is subsequently applied to the condenser lens system 1 in practice, a switch 19 is turned on. Because of the setting to the sufficiently large gain A1, output $\Delta V_{CL}=A1 \cdot \Delta V_{1d}$ is delivered.

It is obvious that $\Delta V_{CL}=0$ holds immediately after application of negative feedback. Then, a switch 20 is turned on. The signal is applied to an amplifier 17 whose gain can be set to A2. The output from the amplifier 17 is applied to a D/A converter 18. The output from the amplifier 16 is multiplied by a factor of A2·r2, where r2 is a signal ratio indicated by data DA2 from the D/A converter 18. The following signal is delivered from the D/A converter 18:

$$\Delta V_{OL}=A2 \cdot r2 \cdot \Delta V_{CL}$$

The signal $\Delta V_{CL}$ obtained in this way is added to the condenser lens control portion 6, while $\Delta V_{OL}$ is applied to the objective lens control portion 8.

If some change occurs in the charged particle beam source, and if the probe current is not stabilized, the probe current $I_p$ and the detected current $I_d$ should vary as follows. However, because of the action of negative feedback applied to the condenser lens system 1, the currents $I_p$ and $I_d$ can be kept substantially constant.

$$I_{p0} \rightarrow I_{p0}+\Delta I_p$$

$$I_{d0} \rightarrow I_{d0}+\Delta I_d$$

The relation of the objective lens current signal $V_{OL}$, which maintains the degree of focus of the particle probe, to the condenser lens control current $V_{CL}$ is given by:

$$V_{OL}=F(V_{CL})$$

We have:

$$dV_{OL}/dV_{CL}=F'(V_{CL})$$

A variation for maintaining the probe current constant is given by:

$$V_{CL0} \rightarrow V_{CL0}+\Delta V_{CL}$$

A variation for maintaining the degree of focus for the signal variation $\Delta V_{CL}$ is given by:

$$V_{OL0} \rightarrow V_{CL0}+\Delta V_{OL}$$

If the variation $\Delta V_{CL}$ in $V_{CL}$ is infinitesimal, the variation $\Delta V_{OL}$ in $\Delta V_{OL}$ can be found, using the aforementioned differential coefficient $F'(V_{CL})$, from:

$$\Delta V_{OL}=F'(V_{CL0})\Delta V_{CL}$$

That is, the variation $\Delta V_{OL}$ is in proportion to the variation $\Delta V_{CL}$ if the signal $\Delta V_{CL}$ is small. Accordingly, if the instrument is so set up that the gain A2 of the amplifier 17 and the signal ratio r2 of the D/A converter 18 satisfy the relation:

$$A2 \cdot r2 = F'(V_{CL0})$$

then the degree to which the particle probe is focused can be kept constant by the use of the signal $\Delta V_{CL}$ that is employed to stabilize the probe current.

While one embodiment of the present invention has been described thus far, the invention is not limited to this embodiment. Rather, various changes and modifications are possible. For example, in the above embodiment, a part of the charged particle beam is used as a detected signal. If the degree to which the particle probe is focused is varied by negative feedback other than the negative feedback using the detection aperture 4, the signal for the negative feedback may be adjusted, and this adjusted signal may be applied to the control portion for the condenser lens system and to the control portion for the objective lens.

As an example, a variation A1e in the emission current $I_e$ in a particle beam emission source is detected, and negative feedback is applied to the extraction voltage $V_{ex}$. In this case, the varying signal $I_e$ is adjusted and used.

In the above-described embodiment, a signal for adjusting the focal distance of the objective lens is added to the lens. It is to be noted that the invention is not limited to this scheme. For example, a signal for adjusting the focal distance of the lens may be added to a control portion for a focus-adjusting auxiliary lens located between the detection aperture 4 and the objective lens 8 or to a control portion for a control lens for adjusting the aperture angle of the beam incident on a specimen. Also, in this case, the object of the present invention can be accomplished. That is, a slight amount of defocus affects the final probe diameter greatly. In contrast, a slight deviation from the optimum aperture angle does not affect the final probe diameter.

The configuration shown in FIG. 3 can be applied to the system shown in FIG. 5 of the above-cited Japanese Patent Laid-Open No. 183044/1989. An example of its application is now described. X-axis detection electrodes arranged symmetrically around a charged particle beam produce output currents $I_{X1}$ and $I_{X2}$, respectively. Y-axis detection electrodes perpendicular to the X-axis detection electrodes produce output currents $I_{Y1}$ and $I_{Y2}$, respectively. Amounts of signals indicating the amounts of shifts of the charged particle beam from the optical axis in the X- and Y-axes are given by:

$$V_X=(X_1-X_2)/(X_1+X_2)$$

$$V_Y=(Y_1-Y_2)/(Y_1+Y_2)$$

These amounts of signals are calculated by an arithmetic unit or the like. An amount of signal corresponding to the magnitude of the beam current is given by:

$$V_T=X_1+X_2+Y_1+Y_2$$

Then, these signals of these amounts are converted into digital signals immediately before start of application of negative feedback. The obtained signals are converted into analog signals to find reference signals $V_{X0}$, $V_{Y0}$, and $V_{T0}$. Signals $V_X$, $V_Y$, and $V_T$ are detected immediately after start of application of negative feedback. The differences between these signals $V_X$, $V_Y$, and $V_T$ and the reference signals $V_{X0}$, $V_{Y0}$, and $V_{T0}$ are given by:

$$\Delta V_X=V_X-V_{X0}$$

$$\Delta V_Y=V_Y-V_{Y0}$$

$$\Delta V_T=V_T-V_{T0}$$

These differential signals are found.

Finally, these are amplified by a sufficiently large factor and used as signals for negative feedback. That is, $\Delta V_X$ and $\Delta V_Y$ are used as signals for correcting beam shifts in the X- and Y-directions, respectively. $\Delta V_T$ is used as a signal for correcting the probe current and as a signal for correcting defocus where the probe current is corrected in this way.

In this example of application and in the case of FIG. 3, negative feedback is described using symbols of digital switches that are opened and closed. Instead, analog switches may be used. That is, a signal for negative feedback may be applied gradually. Similarly, an amplifier whose gain is increased gradually may be used. In this case, even if the differential signals $\Delta V_{1d}$, $\Delta V_X$, $\Delta V_Y$, and $\Delta V_T$ are finally amplified with extremely large degrees of amplification, the signal system will not be saturated. Furthermore, stable negative feedback is possible.

As described thus far, in the present invention, a part of a charged particle beam is detected. In response to the detected signal, a first lens is controlled to maintain constant the current of the charged particle beam made to hit a specimen. In response to the detected signal, a second lens is controlled to adjust the focus of the charged particle beam. Therefore, the current of the charged particle probe directed to the specimen can be kept constant at all times without defocus.

In another embodiment of the invention, a signal $\Delta V_{CL}$ used when negative feedback is applied to the control portion for the first lens according to the detected signal is produced by amplifying the difference between $V_{1d}$ and $V_{1d0}$ ($\Delta V_{1d}=V_{1d}-V_{1d0}$) while maintaining the signal $V_{1d0}$ corresponding to the current detected immediately before application of negative feedback. The signal $V_{1d}$ corresponds to the current detected after the start of negative feedback. A signal $\Delta V_{OL}$ proportional to the feedback signal $\Delta V_{CL}$ supplied to the control portion for the first lens is fed to the control portion for the second lens. Consequently, stabilization of the focus of the charged particle probe can be accomplished with a simple structure. When negative feedback is started, the signal for feedback starts at 0. Therefore, the dynamic range of the signal for feedback can be made wide.

Having thus described my invention with the detail and particularity required by the Patent Laws, what is desired protected by Letters Patent is set forth in the following claims.

What is claimed is:

1. A charged particle beam instrument comprising:
   a charged particle beam source for producing a charged particle beam having a probe current;
   a first focusing means for focusing the charged particle beam and varying the probe current of the charged particle beam impinging on a specimen;
   a second focusing means for varying the degree of focus of said charged particle beam impinging on the specimen;
   a first control portion for controlling said first focusing means;
   a second control portion for controlling said second focusing means;
   a detection aperture for intercepting a part of the current of the charged particle beam at the outer portion of the charged particle beam, the remainder of particle beam passing the aperture detector impinging the specimen; and
   means associated with said detection aperture for producing a detected signal, such that in response to said detected signal the first control portion for said first focusing means maintains constant the probe current of the charged particle beam impinging on the specimen and the second control portion for said second focusing means adjusts the focus of said charged particle beam.

2. The charged particle beam instrument of claim 1, wherein said second focusing means is an objective lens.

3. The charged particle beam instrument of claim 1, wherein said second focusing means is an auxiliary lens located close to an objective lens, and wherein strength of said auxiliary lens is adjusted to adjust the focus of said charged particle beam.

4. The charged particle beam instrument of claim 1, wherein a detection aperture is positioned between said first focusing means and said second focusing means to detect the charged particle beam incident on said aperture.

5. The charged particle beam instrument of claim 1, wherein a signal $\Delta V_{CL}$ used when feedback is applied to the control portion for said first focusing means according to said detected signal is obtained by amplifying the difference $\Delta V_{1d}$ ($=V_{1d}-V_{1d0}$) between a signal $V_{1d}$ corresponding to a current detected alter start of the feedback and a signal $V_{1d0}$ corresponding to a current detected immediately before the application of the feedback while maintaining the signal $V_{1d0}$ corresponding to the signal detected immediately before the application of the feedback.

6. The charged particle beam instrument of claim 5, wherein a signal $\Delta V_{OL}$ proportional to the feedback signal $\Delta V_{CL}$ supplied to the control portion for said first focusing means is simultaneously supplied to the control portion for said second focusing means.

* * * * *

UNITED STATES PATENT AND TRADEMARK OFFICE
CERTIFICATE OF CORRECTION

PATENT NO. : 6,933,512 B2
DATED : August 23, 2005
INVENTOR(S) : Miyuki Matsuya

It is certified that error appears in the above-identified patent and that said Letters Patent is hereby corrected as shown below:

Column 8,
Line 35, "current detected alter" should read -- current detected after --.

Signed and Sealed this

Seventh Day of February, 2006

JON W. DUDAS
*Director of the United States Patent and Trademark Office*